(12) United States Patent
Malfant et al.

(10) Patent No.: US 8,617,435 B2
(45) Date of Patent: Dec. 31, 2013

(54) PHOTOCHROMIC COMPOSITE MATERIAL

(75) Inventors: Isabelle Malfant, Goyrans (FR); Benoit Cormary, Montgiscard (FR); Lydie Valade, Cugnaux (FR)

(73) Assignee: Centre National de la Recherche Scientifique-CNRS, Paris (FR)

( * ) Notice: Subject to any disclaimer, the term of this patent is extended or adjusted under 35 U.S.C. 154(b) by 124 days.

(21) Appl. No.: 13/144,378

(22) PCT Filed: Jan. 6, 2010

(86) PCT No.: PCT/FR2010/050011
§ 371 (c)(1),
(2), (4) Date: Oct. 27, 2011

(87) PCT Pub. No.: WO2010/081977
PCT Pub. Date: Jul. 22, 2010

(65) Prior Publication Data
US 2012/0032123 A1   Feb. 9, 2012

(30) Foreign Application Priority Data

Jan. 13, 2009  (FR) .................................... 09 00126

(51) Int. Cl.
G02B 5/23      (2006.01)
G02F 1/13      (2006.01)
G03F 7/00      (2006.01)
G11B 7/24      (2013.01)

(52) U.S. Cl.
USPC .......... 252/586; 349/2; 369/125; 430/270.11; 977/700; 977/773

(58) Field of Classification Search
USPC ....... 252/586; 977/700, 773; 349/2; 369/125; 430/270.11; 503/200, 201, 218
See application file for complete search history.

(56) References Cited

U.S. PATENT DOCUMENTS 5,821,287 A   10/1998   Hu et al.

FOREIGN PATENT DOCUMENTS

EP   0 592 366 A1   4/1994
WO   2006/019435 A1  2/2006

OTHER PUBLICATIONS

Benoit Cormary, Isabelle Malfant, Lydie Valade, New photochromic xerogels composites based on nitrosyl complexes, J Sol-Gel Sci Technol (2009) 52:19-23.*
David Levy (Photochromic Sol-Gel Materials, Chem. Mater. 1997, 9, 2666-2670.*
Dominik Schaniel, Benoit Cormary, Isabelle Malfant, Lydie Valade, Theo Woike, Bernard Delley, Karl W. Kramerd and Hans-Ueli Gudel,Photogeneration of two metastable NO linkage isomers with high populations of up to 76% in trans- [RuCl(py)4(NO)][PF6]2 . 1/2H2O, Phys. Chem. Chem. Phys., 2007, 9, 3717-3724.*
Levy D: "Photochromic Sol-Gel Materials", Chemistry of Materials, American Chemical Society, Washington, US, vol. 9, No. 12, Dec. 1, 1997, pp. 2666-2670, XP000729200, ISSN: 0897-4756.
Schaniel D. et al.: Photogeneration of two metastable NO linkage isomers with high populations of up to 76% in trans-[RuCl(py)4(NO)][PF6]2-½H2O, Physical Chemistry Chemical Physics, vol. 9, 2007, pp. 3717-3724, XP002542585.
International Search Report, dated Apr. 29, 2010, from corresponding PCT application.

* cited by examiner

*Primary Examiner* — Bijan Ahvazi
(74) *Attorney, Agent, or Firm* — Young & Thompson

(57) ABSTRACT

Sol-gel process for producing a photochromic composite material includes successive stages of hydrolysis, condensation, and drying, in which an alkoxysilane is selected as a precursor, and a ruthenium complex with a nitrosyl ligand is selected as a photochromic complex, and, in combination, the sol-gel process is implemented starting from the selected precursor and photochromic complex, with successive stages of hydrolysis, arrangement in a container of a selected shape, condensation, curing and aging, whereby this latter stage includes a final drying cycle, and for, the curing and aging stages, the pH, temperature and duration are selected so that in the produced xerogel, whose shape is determined by that of the container, the photochromic ruthenium complex with a nitrosyl ligand, in the crystalline state and in the form of nanoparticles, is inserted into the nanopores of the silica matrix, distributed in an at least substantially homogeneous way.

21 Claims, No Drawings

PHOTOCHROMIC COMPOSITE MATERIAL

The invention relates to photochromic composite materials.

Such materials make it possible to put together high-density data optical storage media.

Such an optical storage medium should have a certain number of properties such as a good optical quality, a minimum thickness, excited states with a long service life, and a significant photo-induced change, namely an important modification of the refraction index, whereby the latter is an essential parameter in the holographic technique for data storage. The provision of these properties, in combination, is a restriction limiting the candidate materials for such an optical storage function (see J. Ashley, M-P. Bernal, G. W. Burr, H. Coufal, H. Guenther, J. A. Hoffnagle, C. M. Jefferson, B. Marcus, R. M. Macfarlane, R. M. Shelby, G. T. Sincerbox, "Holographic Data Storage," IBM J. Res. Develop., Vol. 44, 2000, 341).

Different materials have been studied as optical storage media: inorganic materials synthesized in the form of large-size crystals, such as $LiNbO_3$ or $BATiO_3$, or photoreactive composite polymers, in particular the composite that combines a chromophore molecule such as phenanthrenequinone (PQ) in a methyl methacrylate matrix (PMMA), or else a chromophore group such as azobenzenes or spiropyrans. In such cases, the inorganic materials or the photoreactive composite polymers are such that following a light excitation, their optical properties, such as their refraction index, are modified in a reversible way (G. T. Sincerbox, "Holographic Storage: Are We There Yet.".

Studies have also been done on photochromic molecules that have a chemical nitrosyl group, such as sodium nitroprussiate $Na_2[Fe(CN)_5NO].2H_2O$, which has a reversible isomerization, at low temperature, and which entrains a change in color and a modification of the refraction index of the compound. The metastable photoinduced states have a long service life (longer than 347 days). In this type of molecular material, irradiation causes the change in conformation of the nitrosyl ligand. The optical change is localized, the variation of the refraction index is significant, and the change of state speed is suitable relative to the application in question. This type of material thereby has a certain number of limits: the definition of the image is not optimal for the reason that the generated population is only partial; the operating temperature is far from the ambient temperature, and the material comes in the form of monocrystals, with the inherent drawbacks: fragility, a size that is difficult to control (see a) P. Gutlich, Y. Garcia, T. Woike, "Photoswitchable Coordination Compounds," Coord. Chem. Rev., 2001, 839. b) T. Woike, W. Kirchner, G. Schetter, T. Barthel, S. Haussuhl, "New Information Storage Elements on the Basis of Metastable Electronic States," Optics Comm., Vol. 106, 1994, 6. c) M. Imlau, M. Fally, T. Weisemoeller, D. Schaniel, "Holographic Light Scattering in Centrosymmetric Sodium Nitroprusside Upon Generation of Light-Induced Metastable States," Phys. Rev. B, Vol. 73, 2006, 205113).

D. Schaniel, B. Cormary, I. Malfant, L. Valade, T. Woike, B. Delley, K. W. Kramer, H. U. Gudel, "Photogeneration of Two Metastable NO Linkage Isomers with High Populations of up to 76% in trans-$[RuCl(NO)(py)_4][PF_6]_2 \cdot \frac{1}{2}H_2O$," Phys. Chem. Chem. Phys., Vol. 9, 2007, 3717, describes the $[RuCl(NO)(py)_4][PF_6]_2 \cdot \frac{1}{2}H_2O$ complex, which has properties analogous to those described above, but with increased effectiveness. With this photochromic ruthenium complex with a nitrosyl ligand, the switching property produced by the formation of metastable states is linked to the change in conformation of the nitrosyl ligand in the complex. This structural change is accompanied by an important modification of the refraction index. As test specimens of increased effectiveness, it is possible to indicate, for example, that the conversion of the fundamental state to the metastable state is nearly total when the complex is in crystal form and that the operating temperature is higher than before. There remains, however, the task of integrating such a complex, in the form of crystals or powder, into an industrial device of suitable shape. In the case in question that is being considered, this problem has yet to find a satisfactory solution. This is specifically one of the problems to which the invention provides a solution.

Three approach types have been proposed in general for the shaping of the different known photochromic compounds.

The first approach consists of the insertion and the dilution of organic photochromic molecules (diarylethene, spiropyran, for example) in a polymer matrix, with the polymer being condensed. Among the polymers that are used, it is possible to cite polyvinyl alcohol (PVA), polyvinyl pyridine (PVP), and methyl polymethacrylate (PMMA). The photochromic molecules are then dispersed in the form of nanoparticles inside the polymer matrix. This first approach makes possible the reading and writing of data with great precision. The storage density may be significant and the resolution high. By contrast, this first approach has as its limitation its poor heat stability, the weakness of the possible thickness for allowing a three-dimensional optical storage, the existence of strong variations of optical properties based on temperature, aging, and even the deterioration of the medium over read/write/erase cycles. Consequently, this first approach does not make it possible to optimize the quantity of stored data, and the quality and the precision of the storage decrease over time.

The second approach, for inorganic materials such as $LiNbO_3$ or $BATiO_3$ or photochromic molecules that have a chemical nitrosyl group, such as $Na_2[Fe(CN)_5NO]$, consists in the production of monocrystals. The optical qualities that are achieved are excellent, but this approach has the drawback of a reproducibility of limited production, a true mechanical fragility, with the crystals being brittle, and a significant monitoring difficulty of the form that is produced. For these reasons, this approach is not very compatible with the industrial scale.

D. Levy, "Photochromic Sol-Gel Materials," Chem. Master., Vol. 9, 1997, 2666 teaches a third approach, namely the insertion of photochromic molecules in a silica matrix by a sol-gel process (hydrolysis, condensation and drying). An alkoxysilane (such as tetramethoxyorthosilane—TMOS—, vinyltriethoxysilane—VTES—, or tetraethoxyorthosilane—TEOS—) is used as a precursor. By the sol-gel reaction in aqueous solution, the alkoxysilane condenses, and in the presence of photochromic molecules (such as spiropyrans), a composite material is obtained. The silica matrix that is formed has pores of variable nanometric sizes based on the pH of the reaction medium. The photochromic molecules are trapped in these pores. It is possible, by this third approach, to produce plates or monoliths of the desired shape. In addition to the control of the shape that is produced and the possibility of producing shapes of sufficient thickness, this third approach in particular has for advantages the preservation of optical properties of inserted photochromic molecules, heat stability, and the slight variation of the refraction index of the matrix based on the temperature. By contrast, this third approach has for its limit, noted to date, the existence of troublesome interactions between the inserted photochromic molecules and the silica matrix with pores that interfere with the final effectiveness. In contrast, the operating conditions of the stages of the sol-gel process should be controlled if it is desired to be able to obtain a quality composite medium.

The document WO 2006/019435 describes processes for the production of photosensitive microparticles and aqueous compositions that comprise them. The document U.S. Pat. No. 5,821,287 refers to the synthesis of photochromic compounds. The document EP-A-0592366 refers to photochromic compounds.

The problem at the base of the invention consequently consists in producing a photochromic composite material for the high-density data optical storage that, at the same time, either has a manageable shape and size and is resistant, can be thick enough, or transparent, and whose shaping does not negatively affect the switching properties of the monocrystal, i.e., a conversion level on the order of 100%. In addition, the process for production of such a photochromic composite material is energy-efficient (as typically achieved at ambient temperature and pressure) and has the minimum amount of toxic effects on the environment (such as typically by avoiding the use of harmful solvents in favor of water). It is also a process that is reproducible and feasible on the industrial scale.

To this end, the purpose of the invention is to combine the qualities noted by way of experimentation in the photochromic ruthenium complex with a nitrosyl ligand [RuCl(NO)(py)$_4$][PF$_6$]$_2$.½H$_2$O described in D. Schaniel, B. Cormary, I. Malfant, L. Valade, T. Woike, B. Delley, K. W. Kramer, H. U. Gudel, "Photogeneration of Two Metastable NO Linkage Isomers with High Populations of Up to 76% in Trans-[RuCl(NO)(py)$_4$][PF$_6$]$_2$.½H$_2$O," Phys. Chem. Chem. Phys., Vol. 9, 2007, 3717 (complete switching to the solid state), with advantages obtained by the third previously-mentioned shaping approach (insertion of photochromic molecules in a silica matrix by a sol-gel process).

The invention is noteworthy by virtue of the fact that the qualities that the photochromic ruthenium complexes with a nitrosyl ligand offer are, surprisingly enough, preserved by the shaping in a silica matrix by the sol-gel process.

For this purpose, and according to a first aspect, the purpose of the invention is a sol-gel process for the production of a photochromic composite material, in which:
  There is a precursor,
  There is a photochromic complex,
  A sol-gel process is implemented starting from the precursor and the photochromic complex, with successive stages of hydrolysis, condensation, and drying,
characterized by the fact that:
  An alkoxysilane is selected as a precursor,
  A ruthenium complex with a nitrosyl ligand is selected as a photochromic complex, and, in combination,
  The sol-gel process is implemented starting from the selected precursor and photochromic complex, with successive stages of hydrolysis, arrangement in a container of a selected shape, condensation (or polymerization or gelling), curing and aging, whereby this latter stage includes a final drying cycle, and
  For the stages of curing and aging, the pH, the temperature and the duration are selected so that in the xerogel that is produced, whose shape is determined by that of the container, the photochromic ruthenium complex with a nitrosyl ligand, in the crystalline state and in the form of nanoparticles, is inserted into the nanopores of the silica matrix, distributed in an at least substantially homogeneous way.
According to other characteristics of the process:
  The precursor is selected from the group that comprises tetramethoxyorthosilane—TMOS—, vinyltriethoxysilane—VTES—, tetraethoxyorthosilane—TEOS—, or the alkoxides M(OR)x, where M is a metal and R is an alkyl group;
  The photochromic complex is selected from the group that comprises [RuCl(NO)(py)$_4$][PF$_6$]$_2$.½H$_2$O and [RuY(NO)(py)$_4$]X$_2$, in which Y is Cl, Br, or OH, and X is selected from the family that comprises Br, Cl, PF$_6$ and BF$_4$;
  An acidic pH (<7) is selected for the stages of curing and aging;
  In the presence of acetonitrile, the curing stage lasts on the order of one week at a temperature on the order of 55° C., in a closed atmosphere, whereas in the presence of water, the curing stage lasts on the order of 72 hours at ambient temperature;
  The aging stage lasts on the order of one week at a temperature on the order of 55° C.

This process is energy-efficient because it can be carried out at ambient temperature and pressure. It exhibits minimal harmful effects on the environment for the reason that it makes it possible to avoid the use of harmful solvents in favor of water.

This process is ultimately reproducible and feasible on the industrial scale.

According to a second aspect, the purpose of the invention is the photochromic composite material that is obtained by the process that was just described.

According to other characteristics of this photochromic composite material, the xerogel that is produced has a shape that is determined by that of the container and comprises the photochromic ruthenium complex with a selected nitrosyl ligand, in the crystalline state and in the form of nanoparticles, inserted into the nanopores of the silica matrix, distributed in an at least substantially homogeneous way.

According to other characteristics:
  The material comes in the shape of a monolith or in the shape of a plate of desired thickness;
  The mean size of the nanopores of the silica matrix is between 2 and 15 nm;
  The most numerous particles of the nanocrystals of the photochromic complex are between 2 and 4 nm.

All at the same time, this photochromic composite material has a manageable shape and size, and is resistant, thick enough when this is desired for larger storage capacities, and transparent.

Finally, the shaping of this material by the sol-gel process with a silica matrix does not negatively affect the switching properties that exist on the monocrystal of the ruthenium complex, namely a rate of conversion on the order of 100%.

According to a third aspect, the purpose of the invention is a high-capacity optical memory medium comprising at least one photochromic composite material as was just described.

Such a medium offers optical storage qualities, in particular capacity, clearly superior to that which has been proposed to date.

According to other characteristics of this media with optical memory:
  Its photoinduced population is close to that of monocrystals of the photochromic complex;
  Its temperature of use is close to ambient temperature;
  It has a complete reversible change of color after irradiation;
  Its metastable states have a service life that is longer than 9 years.

The invention will be better understood from reading the description of several embodiments that will follow.

As indicated above, the invention has three aspects:
- A sol-gel process for production of a photochromic composite material,
- Such a photochromic composite material, characterized in that it is obtained by this process, and
- A high-quality optical memory medium, in particular capacity, comprising at least one such photochromic composite material.

The process for production of a photochromic composite material according to the invention uses the method (or the reaction) that is known under the name of "sol-gel."

The principles of the latter are known or are easily within the scope of one skilled in the art. Refer in particular to the document of D. Levy, "Photochromic Sol-Gel Materials," Chem. Master., Vol. 9, 1997, 2666.

It is known that the sol-gel method comprises the following successive stages:
- Hydrolysis,
- Condensation, or, otherwise designated, polymerization or gelling,
- Drying.

In the process for the production of a photochromic composite material according to the invention, an alkoxysilane is selected as precursor, and this precursor is available.

In contrast, a ruthenium complex with a nitrosyl ligand is selected as a photochromic complex, and this complex is available.

In one embodiment, tetramethoxyorthosilane—TMOS—is used as a precursor.

In other possible embodiments, vinyltriethoxysilane—VTES—, and even tetraethoxyorthosilane—TEOS—, or the functional equivalent, more generally the alkoxides $M(OR)_x$, where M is a metal and R is an alkyl group, is used as a precursor.

In one embodiment, $[RuCl(NO)(py)_4][PF_6]_2 \cdot \tfrac{1}{2}H_2O$ is used as a photochromic complex.

In another possible embodiment, $[RuY(NO)(py)_4]X_2$, in which Y=Br, OH with X=Br, Cl, $PF_6$, $BF_4$ and Y=Cl with X=Br, Cl, $BF_4$ or the functional equivalent, is used as a photochromic complex.

According to the invention, the sol-gel process is implemented starting from the selected precursor and the photochromic complex, with successive stages of hydrolysis, arrangement in a container of a selected shape, condensation (or polymerization or gelling), curing and aging, whereby this latter stage includes a final drying cycle.

In addition, for the curing and aging stages, the pH, the temperature and the duration are selected so that in the xerogel that is produced, whose shape is determined by that of the container, the photochromic ruthenium complex with a nitrosyl ligand, in the crystalline state and in the form of nanoparticles, is inserted into the nanopores of the silica matrix, distributed in an at least substantially homogeneous way.

The operating stages are produced at mild temperatures and pressure, close to ambient.

In the stage for hydrolysis of alkoxide, the hydrolysis of the alkoxide can be total if the proportions of water, pH and temperature are selected for this purpose. All of the OR groups are then replaced by OH groups.

To implement this stage, alkoxide is mixed with methanol, and this mixture is stirred for the necessary amount of time, for example on the order of 5 minutes. Hydrolysis is begun by the addition of distilled water.

After a certain time, for example on the order of 2 minutes, the selected photochromic complex, itself in solution, is added to the precursor.

Stirring is continued for the necessary time, for example on the order of 10 minutes.

In one embodiment, the proportions are 1 ml of tetramethoxyorthosilane (TMOS) and 1.2 ml of methanol and twice this, or 2.4 ml of distilled water.

The photochromic complex as selected is used in an acetonitrile solution in the case of $[RuCl(NO)(py)_4][PF_6]_2 \cdot \tfrac{1}{2}H_2O$, whereby this complex is not soluble in water or in water in the case of $[RuY(NO)(py)_4]X_2$, with X=Cl, Br.

Then, after the hydrolysis stage, the precursor is used as selected, and the photochromic complex is used as selected and in solution, in a container of the selected shape, which conditions the shape of xerogel that will be produced, monolithic or plate.

For example, it is possible to use a container such as a tube with hemolysis for forming a monolith and a container such as a flat-bottomed box for forming a plate with the desired thickness.

The stage of condensation (or polymerization or gelling) leads to the formation of oxygen bridging with the elimination of the water or alcohol molecule. At the end of this stage, the bridging oxygen atoms make possible the formation of a three-dimensional silica network that is obtained according to the following reaction balance:

The condensation stage leads to the production of a gel.

When $[RuCl(NO)(py)_4][PF_6]_2 \cdot \tfrac{1}{2}H_2O$ is implemented as a photochromic complex and when the precursor, such as TMOS, is in a mixture that contains acetonitrile, the condensation is longer and the appearance of the moist gel only occurs later. If the subsequent curing stage is too fast or is carried out in an open atmosphere, it is possible that the gel that is obtained is not homogeneous and photochromic complex microcrystals are dispersed in the matrix.

By curing and then aging stages, this gel is stabilized: the polymerization begun previously continues, while the solvent that is inside the gel is expelled.

For these stages of curing and aging, the pH, the temperature and the duration are selected so that the finally produced xerogel, whose shape is determined by the container, and the photochromic complex, in the crystalline state and in the form of nanoparticles, is inserted into the nanopores of the silica matrix, distributed in an at least substantially homogeneous way.

Thus, in one embodiment, the selected pH is on the order of 5 in the case of the photochromic complex $[RuCl(NO)(py)_4][PF_6]_2 \cdot \tfrac{1}{2}H_2O$ and on the order of 5.6 in the case of $[RuCl(NO)(py)_4]Br_2$.

In one embodiment, the curing stage lasts in the first case on the order of one week at a temperature on the order of 55° C., in a closed atmosphere, because of the presence of acetonitrile. In the second case, the curing stage lasts on the order of 72 hours at ambient temperature.

In one embodiment, the aging stage—in the first case and in the second case—lasts on the order of one week at a temperature on the order of 55° C.

The end of the aging stage allows a drying cycle by which the silica gel is densified, and the rest of the solvent is eliminated.

The drying by slow evaporation causes a contraction of the silica network that can reduce the volume of gel (for example a loss of volume of ⅕) and can lead to the formation of a xerogel, in the shape of a monolith or plate. In contrast, if the drying occurs under tough conditions, beyond the critical point of the solvent, the moist gel shrinks very little, and not a xerogel as desired, but rather an aerogel, is obtained.

If the curing and aging stages are too fast, undesirable cracks or fractures may occur in the material that is produced.

When a water/methanol mixture (without acetonitrile) is used, the higher the concentration of the photochromic complex, the more intense the color of the gel. In contrast, when a water/methanol/acetonitrile mixture is used, when the photochromic complex concentration exceeds 30 mmol·$L^{-1}$, the matrix is saturated by the complex and crystals and powder form inside and around the xerogel.

According to the invention—and as has been illustrated previously—for the stages of curing and aging, the pH, the temperature and the duration are selected so that within the xerogel that is produced, whose shape is determined by the container, the photochromic complex is in the crystalline state and in the form of nanoparticles and is inserted into the nanopores of the silica matrix, themselves distributed in an at least substantially homogeneous way.

With the process as was just described, photochromic composite materials are obtained that are homogeneous, transparent, easily modelable, and stable in normal conditions of temperature and pressure. Thus, it was noted that the xerogels do not show deterioration after four months and even up to seven months. These materials have an excellent resistance to laser radiation, a mechanical resistance that is analogous to that of glass, and a good resistance to solvents.

As already indicated, it is possible to produce photochromic composite materials in a monolithic shape of 1 to 2 cm in length or in a plate shape of 1 to 3 $cm^2$ and with the desired thickness.

The mean size of the nanopores of the silica matrix produced without acidic or basic catalysis is between 2 and 15 nm. Their distribution is homogeneous.

The photochromic complexes come in the form of nanocrystals. The particles that consist of between 2 and 4 nm are the most numerous.

Taking into account sizes and intermolecular distances in play, it turns out that the smallest nanopores of the silica matrix contain one or two ruthenium molecules with its counter-ions.

The analyses made on the composite materials obtained during the tests have shown that the particles are well diluted in the matrix and that the objects of nanometric size that are in the nanopores are well constituted by the photochromic complex.

The photochromism of the composite materials obtained, as follows, is demonstrated in the case of a silica matrix with which a photochromic complex [RuCl(NO)(py)$_4$][PF$_6$]$_2$·½H$_2$O is associated.

A sample of this material is placed in a cryostat, and then it is irradiated for 2 hours at a temperature on the order of 100 K. The sample is removed from the cryostat as quickly as possible. A change in color of the sample that passes from the color orange—color in the basic state—to the color green—color in the irradiated state—is noted.

When the sample is removed from the cryostat, the rise in temperature is very fast, and the relaxation begins after only 1 minute. After several minutes, the sample returns to its orange color.

Thus, the photochromic composite materials that are produced have the characteristic of a complete reversible change of their color after irradiation. An estimate of the photoinduced population—on the order of 36%—shows that it is close to the one observed on monocrystals. These photochromic composite materials can be implemented at temperatures that are close to ambient temperature. As for the metastable states, their service life is longer than 9 years.

These photochromic composite materials are therefore perfectly well suited to the composition of high-quality optical memory media, in particular involving the capacity.

The invention claimed is:

1. A sol-gel process for the production of a photochromic composite material, comprising the steps of:
   selecting an alkoxysilane as a precursor,
   selecting a ruthenium complex with a nitrosyl ligand is selected as a photochromic complex, and, in combination,
   starting the sol-gel process by providing the selected precursor and the selected photochromic complex, with successive stages of hydrolysis, arrangement in a container of a selected shape, condensation, curing and aging, whereby a latter stage includes a final drying cycle, and
   for the stages of curing and aging, pH, temperature and duration are selected so xerogel that is produced, whose shape is determined by that of the container, the photochromic ruthenium complex with the nitrosyl ligand, in a crystalline state and in form of nanoparticles, is inserted into nanopores of silica matrix, distributed in an at least substantially homogeneous way.

2. The process according to claim 1, wherein the precursor is selected from the group consisting of tetramethoxyorthosilane (TMOS), vinyltriethoxysilane (VTES), tetraethoxyorthosilane (TEOS), and alkoxides M(OR)x, wherein M is a metal and R is an alkyl group.

3. The process according to claim 2, wherein total hydrolysis of the alkoxide is achieved, with all of OR groups being replaced by OH groups.

4. The process according to claim 2, wherein the alkoxide is mixed with methanol, and the mixture is stirred.

5. The process according to claim 1, wherein the photochromic complex is selected from the group consisting of [RuCl(NO)(py)$_4$][PF$_6$]$_2$·½H$_2$O and [RuY(NO)(py)$_4$]X$_2$, wherein Y is Cl, Br, or OH, and X is selected from the group consisting of Br, Cl, PF$_6$ and BF$_4$.

6. The process according to claim 1, wherein stages of the sol-gel process are produced at mild temperature and pressure, close to ambient temperature and pressure.

7. The process according to claim 1, wherein after beginning of the hydrolysis stage, the selected photochromic complex in solution, is added to the precursor.

8. The process according to claim 1, wherein the selected photochromic complex in solution is used in water or, acetonitrile.

9. The process according to claim 1, wherein the container in the form of a tube or a flat-bottomed box is used, depending on whether it is desired to produce a monolith or a plate.

10. The process according to claim 1, wherein an acidic pH<7 is selected for the stages of curing and aging.

11. The process according to claim 1, wherein in presence of acetonitrile, the curing stage lasts on the order of one week at a temperature on the order of 55° C., in a closed atmosphere.

12. The process according to claim 1, wherein in presence of water, the curing stage lasts on the order of 72 hours at ambient temperature.

13. The process according to claim 1, wherein the aging stage lasts on the order of one week at a temperature on the order of 55° C.

14. A photochromic composite material produced by the process according to claim 1, wherein xerogel that is produced has a shape that is determined by that of the container and comprises the photochromic ruthenium complex with the nitrosyl ligand, in a crystalline state and in form of nanoparticles, is inserted into nanopores of silica matrix, distributed in an at least substantially homogeneous way.

15. The photochromic chromic composite material according to claim 14, wherein the photochromic composite material is in the shape of a monolith or in the shape of a plate of a desired thickness.

16. The photochromic composite material according to claim 14, wherein a mean size of the nanopores of silica matrix is between 2 and 15 nm.

17. The photochromic composite material according to claim 14, wherein most numerous particles of the photochromic complex nanocrystals are between 2 and 4 nm.

18. A high-quality optical memory medium comprising at least one photochromic composite material according to claim 14, wherein a photo-induced population of the at least one photochromic composite material is close to photochromic complex monocrystals.

19. An optical memory medium according to claim 18, wherein a temperature is close to the ambient temperature.

20. The optical memory medium according to claim 18, having a complete reversible change of color after irradiation.

21. The optical memory medium according to claim 18, having metastable states with a service life greater than 9 years.

* * * * *

UNITED STATES PATENT AND TRADEMARK OFFICE
CERTIFICATE OF CORRECTION

PATENT NO.      : 8,617,435 B2
APPLICATION NO. : 13/144378
DATED           : December 31, 2013
INVENTOR(S)     : Malfant et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this
Twenty-second Day of September, 2015

Michelle K. Lee
*Director of the United States Patent and Trademark Office*